United States Patent [19]

Seedorf et al.

[11] Patent Number: 5,719,022
[45] Date of Patent: Feb. 17, 1998

[54] PROCESS FOR DIAGNOSING NON-INSULIN-DEPENDANT DIABETES MELLITUS

[75] Inventors: Luitgard Seedorf, Frederiksberg, Denmark; Hans-U. Häring; Axel Ullrich, both of München, Germany

[73] Assignee: Max-Planck-Gesellschaft zur Förderung der Wissenschaften E.V., Munich, Germany

[21] Appl. No.: 140,110

[22] PCT Filed: Apr. 30, 1992

[86] PCT No.: PCT/EP92/00949

§ 371 Date: Nov. 21, 1994

§ 102(e) Date: Nov. 21, 1994

[87] PCT Pub. No.: WO92/19769

PCT Pub. Date: Nov. 12, 1992

[30] Foreign Application Priority Data

May 2, 1991 [DE] Germany .............. 41 14 365.5

[51] Int. Cl.[6] .............. C12Q 1/68; C12P 19/34; C07H 21/02; C07H 21/04
[52] U.S. Cl. .............. 435/6; 435/91.2; 536/23.1; 536/24.3; 536/24.33
[58] Field of Search .............. 435/6, 91.2, 7.1; 536/23.1, 24.3, 24.31, 24.33

[56] References Cited

U.S. PATENT DOCUMENTS 4,965,189  10/1990  Owerbach .............. 435/6

FOREIGN PATENT DOCUMENTS 0 314 500  5/1989  European Pat. Off. .

OTHER PUBLICATIONS

Mosthof et al. EMBO J. 9: 2409–2413, 1990.
Mosthof et al. PNAS 88: 4728–4730, 1991.
Seino et al. Biochemical and Biophysical Research Communications 159: 312–316, 1989.
Ullrich et al. Nature 313: 756–761, 1985.

Primary Examiner—W. Gary Jones
Assistant Examiner—Dianne Rees
Attorney, Agent, or Firm—Lyon & Lyon LLP

[57] ABSTRACT

To diagnose non-insulin dependent diabetes mellitus or a genetically conditioned disposition thereto, examinations are made of tissue cells, especially skeletal muscle cells, from the person concerned for the presence of the human insulin receptor type B (HIR-B). This examination is preferably conducted with the aid of specific oligonucleotides as primers in a PCR amplification reaction of cDNA obtained from tissue RNA which enables a distinction to be made between HIR-A and HIR-B RNA.

4 Claims, 2 Drawing Sheets

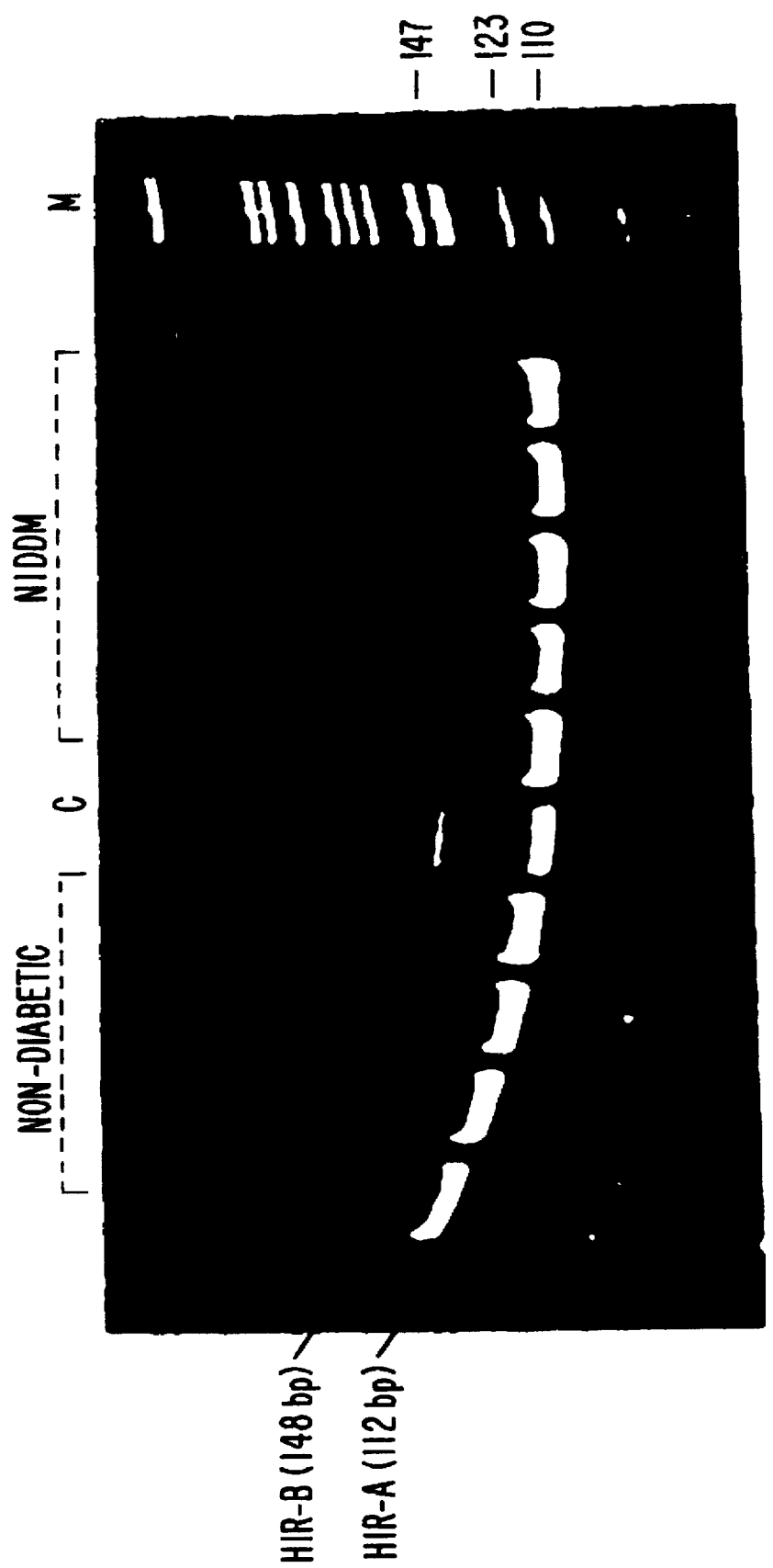

SEQUENCE LISTING ( 1 ) GENERAL INFORMATION:

( i i i ) NUMBER OF SEQUENCES:3

( 2 ) INFORMATION FOR SEQ ID NO: 1:

( i ) SEQUENCE CHARACTERISTICS:

(A) LENGTH: 23
        (B) TYPE: nucleic acid
        (C) STRANDEDNESS: single
        (D) TOPOLOGY: linear (ii) SEQUENCE DESCRIPTION: SEQ ID NO: 1:

ACGTCCCGTC AAAATATTGC AAA					23

(2) INFORMATION FOR SEQ ID NO: 2:

(i) SEQUENCE CHARACTERISTICS:
        (A) LENGTH: 122
        (B) TYPE: nucleic acid
        (C) STRANDEDNESS: single
        (D) TOPOLOGY: linear (ii) SEQUENCE DESCRIPTION: SEQ ID NO: 2:

GCACAACCAG AGTGAGTATG AGGATTCGGC CGGCGAATGC TGCTCCTGTC		50

CAAAGACAGA CTCTCAGATC CTGAAGGAGC TGGAGGACTC CTCGTTTAGG		100

AAGACGTTTG AGGATTACCT GC					122

(2) INFORMATION FOR SEQ ID NO: 3:

(i) SEQUENCE CHARACTERISTICS:
        (A) LENGTH: 22
        (B) TYPE: nucleic acid
        (C) STRANDEDNESS: single
        (D) TOPOLOGY: linear (ii) SEQUENCE DESCRIPTION: SEQ ID NO: 3:

TGGCCGTGCC CACGGTGGCA GC					22

PROCESS FOR DIAGNOSING NON-INSULIN-DEPENDANT DIABETES MELLITUS

This application is a 371 application of PCT/EP 92/00949 filed Apr. 30, 1992.

BACKGROUND OF THE INVENTION

1. Field of the Invention

The invention concerns a process for the diagnosis of nondiabetes mellitus or a genetically conditioned disposition to it.

2. Description of the Prior Art

Type 2 diabetes (noninsulin-dependent diabetes mellitus, NIDDM) has strongly increased in the population in recent decades. There is, therefore, a great interest in providing an easily implemented possibility for diagnosing this diabetes early or, if possible, to be able to detect a genetically conditioned disposition to it before the actual outbreak of the disease.

The task of the present invention was to prepare a process for this that makes it possible to determine rapidly and precisely whether the genetic basis for the disease is present in a patient.

This task was solved by the process according to the invention for diagnosing noninsulin-dependent diabetes mellitus or a genetically determined disposition to it, in which we test cells, especially skeletal muscle cells, of patients for the presence of type B human insulin receptors (HIR-B).

The process according to the invention is based on the surprising recognition that very specific differences can be detected in the presence of the two forms of insulin receptors (HIR-A, HIR-B) in the cells of diabetics in comparison with healthy persons.

Both forms of the receptors have been known for a long time, and research on them has been described by von Mosthaf et al., *EMBO Journal*, vol. 9, No. 8, pp 2409–2413 (1990) as well as in earlier literature referred to there, especially Ebina et al., *Proc. Natl. Acad. Sci. USA* 84 (1987), pp. 704–708; Ullrich et al.,

*Nature* 313 (1985), pp. 756–761; S. Seino and F. L. Bell, *Biochem. Biophys. Res. Common.* 159 (1989), pp. 312–316), and Y. Yarden and A. Ullrich, *Annu. Rev. Biochem.* 57 (1988), pp. 443–478. It was established in them that there are two different forms of receptors, called A and B, both of which consist of equal $\alpha$ and $\beta$ subunits connected with disulfide bonds, where there is a difference, however, in that the type B $\alpha$ subunits have an insertion of 12 amino acids in the region of the C terminal. Since only a single gone can be identified for an insulin receptor, the suspicion was close at hand that a posttranscriptional mechanism is involved in the origin of the two different forms, A and B. Is was further established that the 12 amino acid insert of the B form is coded by a separate exon, and both forms arise from alternative splicing of the primary transcript. It was also established in this regard that the presence of HIR-A and HIR-B RNA depends, both as to amount and in principle, on the tissue. It was also found that the two receptor forms have different binding characteristics for insulin.

SUMMARY OF THE INVENTION

In the framework of the present invention, it has now been established that especially in skeletal muscles, but also in other types of tissue cells, there is specifically in NIDDM patients or persons with a genetically conditioned disposition to it, a nearly equal amount of type A and type B of the human insulin receptor, while in healthy people, only type A receptors are found in the same cells. This is in contrast to some other types of cells in which both receptor types can exist even in healthy people, as can be seen from the literature cited above. In contrast to tissue cells, for example, in human blood cells there is no apparent difference between nondiabetic persons and NIDDM patients. In both cases, there are only type A receptors present, while type B receptors cannot be detected.

In the process according to the invention, all methods can be used in principle that permit a distinction to be made between the two receptor types. Tissue cells for this can be obtained in a known manner, especially by biopsy of patients.

In a preferred implementation of the process according to the invention, we proceed in such a manner that the test for the presence of type B receptors in skeletal muscles is performed with the aid of specific oligonucleotides, by which, when used in a PCR amplification reaction, the cDNA coding DNA for HIR-A and B, is amplified from the RNA obtained from cells. For this, RNA from skeletal muscle tissue is first prepared in a known manner, from which then, likewise in a known manner, cDNA is synthesized.

Here especially, the RNA can be prepared according to a method we have developed ourselves, which produces sufficient amounts of mRNA even from the smallest amounts of tissue (20–40 mg) and is described in Example 1b).

The A RNA obtained is then used for cDNA synthesis. The cDNA is advantageously primed specifically with an oligonucleotide that corresponds to the sequence of the complementary strand of nucleotides 2858–2879 of the cDNA sequence of the human insulin receptor A (numbering according to Ullrich et al. in *Nature* 313 (1985), pp. 756–761). synthesis of the first strand of the cDNA is performed, for example, as described in Sambrook et al. (1989, CSH Laboratory Press, 2nd edition).

The cDNA is then subjected without further purification to several cycles (e.g. about 40) of the polymerase chain reaction. Advantageously, oligonucleotides serve as primers that flank the insertion site for the nucleotide 36 inserted for receptor B. They are thus selected in such a way that one oligonucleotide hybridizes with the sequence upstream from the insertion site and a second oligonucleotide with the sequence downstream from it. Here the sequence of the first oligonucleotide is identical to the sequence of the RNA (with T instead of U), the second oligonucleotide, in contrast, is identical to the sequence of the complementary strand. The first oligonucleotide corresponds in a preferred implementation of the invention to nucleotides 2136–2257 of the human insulin receptor A, the second to the complementary sequence of nucleotides 2327–2348. The reaction was performed as described in Mosthaf at al. (*EMBO J.* 9, pp. 2409–2413, 1990), and gives specific DNA fragments with 112 (HIR-A) and 148 (HIR-B) base pairs when used with the preferred oligonucleotides.

In the presence of cDNA of both receptor variants, two amplification products are then obtained by the PCR reaction, but if only mRNA of type A is present, only one amplification product is obtained.

The presence of an amplification product for HIR-A can also be used as a positive control in the investigation, likewise the amount of HIR-B in comparison with HIR-A can be estimated by it, in which case in the presence of clear amounts of HIR-B in comparison with HIR-A one must assume the presence of noninsulin-dependent diabetes mellitus or a genetically-conditioned disposition to it.

The process in accordance with the invention makes it possible to determine, in a simple way, through rapidly performing a PCR reaction on RNA isolated from tissue and cDNA obtained from it, whether HIR-B RNA has been formed in the tissue, which indicates the presence of NIDDM or a disposition to it, or whether only HIR-A RNA is present, from which it can be concluded that neither NIDDM nor a special disposition to it is present in the patient.

An additional object of the invention is oligonucleotides that include the preferred primary sequence for use in both the cDNA synthesis from RNA from tissue cells and in the PCR reaction.

BRIEF DESCRIPTION OF THE DRAWINGS

The present invention will be further explained in the following example in connection with the diagrams, where:

FIG. 2 shows a comparison test in which blood cells are studied in a corresponding manner.

DESCRIPTION OF PREFERRED EMBODIMENTS

Example a) Tissue Samples

Figure 1:
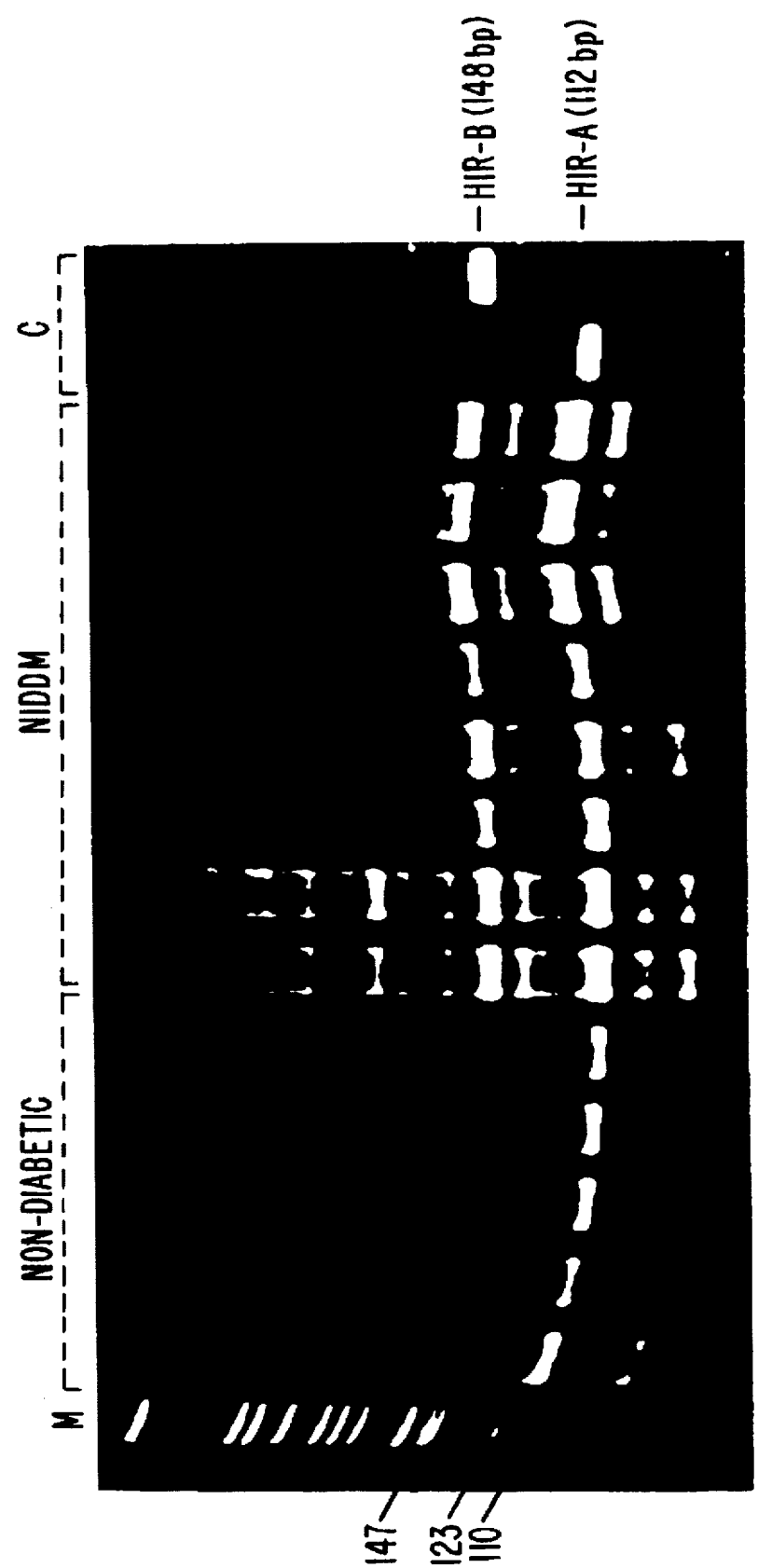
FIG. 1 shows the PCR products separated by electrophoresis separated obtained starting from skeletal tissues from healthy persons and from patients with NIDDM.

Skeletal muscle (musculus gastroenaemius) samples were obtained from diabetic (N=10) and nondiabetic N=6) patients between 60–80 years of age after leg amputations or biopsies. All the samples were cut into small pieces of 0.3 g immediately after the operation, frozen in liquid nitrogen, and kept at −80° C. The muscle samples were subjected to a quality control with evaluation by the following means:

1. Microscopy, electron microscopy, and histochemical quality of the tissue,
2. Enzymatic activity of lactate dehydrogenase EC 1.1.1.27 (LDH), phosphofructokinase EC 2.7.1.11 (PFK), phosphoglyceratekinase EC 2.7.2.3 (PGK) and phosphoglucomutase EC 2.7.5.1 (PGM), and
3. Test for noncollagen protein (NCP) in the normal range of muscle tissue.

The methodology and the morphological and enzymatic determinations are presented in Obermaier-Kusser, et al., *J. Biol. Chem.* 164 (1989), pp. 9497–9503.

Blood samples (5 mL) were taken from 5 NIDDM patients and 5 controls the morning after a 12-h fasting period, mixed with EDTA to prevent coagulation, and immediately thereafter frozen in liquid nitrogen.

b) RNA Preparation

For this, 0.02–1 g of frozen muscle tissue was homogenized with a Polytron in 1 mL of buffer A (0.5M NaCl, 1% SKS, 10 mM tris-HCl Ph 7.5, 1 Mm EDTA, 200 µg/mL proteinase K) and then incubated for 1 h at 37° C. After addition of 210–50 µL of an oligo(dT)cellulose suspension (in buffer A), the sample was shaken for 1h at 37° C.

The mRNA bound to the oligo (dT) cellulose was concentrated by briefly centrifuging in a table centrifuge, washed twice with buffer B (0.5M NaCl, 0.2% SDS, 10 mM tris-HCl pH 7.5, 1 mM EDTA, 1 mM PMSF), and then once with buffer C (0.5M NaCl, 10 mM tris-HCl pH 7.5, 1 mM EDTA). The mRNA was extracted from the oligo (dT) cellulose with 3 washings of 20 µL $H_2O$ each, then heated 5 min to 68° C. and rapidly cooled on ice.

To isolate RNA from blood, 5 mL of blood were diluted twice with a solution of guanidine thiocyanate to a final concentration, homogenized, and precipitated with LiCl, as described in Ullrich et al., *Science* 196 (1977), p. 1313.

c) cDNA Synthesis and Polymerase chain Reaction (PCR)

5–10 µg of total RNA were used for the cDNA synthesis. The cDNA was specifically primed with an oligonucleotide that includes nucleotides 2858–2879 of the human insulin receptor A sequence (Ullrich et al., *Nature* 313 (1985), pp. 756–761). First-level cDNA synthesis was performed essentially in accordance with Sambrook et al., CSH Laboratory Press, 2nd edition (1989) in a total volume of 20 µL of 50 mmol/L KCl, 10 mmol/L tris-HCl pH 8.3, 4 mmol/L mg $Cl_2$, 1 mmol/L dNTPs, 10 µg/mL BSA (beef serum albumin), 50 pmol primer, and 500 U reverse transcriptase by incubating for 1 h at 37° C. The reaction product was subjected without further purification to 40 cycles of a PCR reaction. The PCR was performed as described in Mosthaf et al., *EMBO J.* 9 (1990), pp. 2409–2413, using oligonucleotides that flank the insertion site of the 12 amino-acid insert. The oligonucleotides used represented nucleotides 2136–2257 and the complementary sequence of nucleotides 2327–2348 of the human insulin receptor sequence (Ullrich, supra) and led to formation of specific fragments of 112 (HIR-A) and 148 (HIR-B) base pairs (see FIG. 1 and FIG. 2). A PCR analysis of HIR-A and HIR-B sequences from muscle samples from nondiabetic and diabetic (NIDDM) persons is shown in FIG. 1. The control trace (c) contains PCR fragments, that were obtained from cloned HIR-A or HIR-B-cDNA. Fragments, which do not travel at equivalent height to HIR-A or HIR-B controls, show unspecific or single stranded by-products. A PCR analysis of HIR-A and HIR-B sequences in human blood cells are shown in FIG. 2. The control trace (C) contains a mixture of PCR fragments that were obtained from cloned HIR-A and HIR-B cDNA. Trace (M) contains a size marker in both diagrams. From this example, it is clear that in patients with NIDDM it is possible, with the aid of a PCR analysis or skeletal muscle, to detect the presence of HIR-B and thereby clearly distinguish them from healthy persons. In blood dells, no distinction is possible here.

---

We claim:

1. A process for diagnosing non-insulin dependent diabetes mellitus (NIDDM) or a genetic predisposition to NIDDM, comprising testing skeletal muscle cells for the presence of transcripts encoding type B human insulin receptors (HIR-B);

further comprising the step of determining the ratio of HIR-B mRNA to HIR-A mRNA expression, wherein a ratio of about 1:1 is indicative of NIDDM or susceptibility to NIDDM;

wherein said cells are taken from a person suspected of having NIDDM or wherein said cells are taken from a person suspected of being susceptible to NIDDM.

2. A process according to claim 1, comprising determining the level of accumulation of HIR-B mRNA in a individual suspected of having NIDDM or in an individual suspected of being susceptible to NIDDM by isolating RNA from skeletal muscle cells of said individuals, reverse transcribing said RNA to cDNA, amplifying said cDNA by PCR amplification using oligonucleotide primers specific to the insulin receptor gene (HIR), wherein said oligonucleotide primers amplify fragments diagnostic of the alternatively spliced transcripts of said gene, type A human insulin receptor (HIR-A) mRNA and HIR-B mRNA, and determining the ratio of HIR-B mRNA expression to HIR-A expression by comparing the amounts of fragments amplified, wherein a ratio of about 1:1 is indicative of NIDDM or a susceptibility to NIDDM.

3. A process according to claim 2, wherein an oligonucleotide primer is used which is complementary to nucleotides 2858–2879 of the cDNA sequence of HIR-A.

4. A process according to claim 2 or 3, wherein a first and second oligonucleotide primer is used and wherein said first oligonucleotide primer is complementary to nucleotides 2327–2348 of the cDNA sequence of HIR-A and said second oligonucleotide primer is complimentary to nucleotides 2136–2257 of the cDNA sequence of HIR-A.

* * * * *